US00PP11299P

United States Patent [19]

Walden

[11] Patent Number: Plant 11,299

[45] Date of Patent: Mar. 21, 2000

[54] FLORIBUNDA ROSE PLANT NAMED 'JACMEBUB'

[75] Inventor: John K. Walden, Thousand Oaks, Calif.

[73] Assignee: Bear Creek Gardens, Inc., Medford, Oreg.

[21] Appl. No.: 09/052,806

[22] Filed: Mar. 31, 1998

[51] Int. Cl.[7] ..... A01H 5/00

[52] U.S. Cl. ..... Plt./149

[58] Field of Search ..... Plt./148, 149, 150, Plt./128, 129

[56] References Cited

U.S. PATENT DOCUMENTS

P.P. 2,321 11/1963 Boerner ..... Plt./141
P.P. 8,942 10/1994 Olesen et al. ..... Plt./121

*Primary Examiner*—Howard J. Locker
*Attorney, Agent, or Firm*—Klarquist Sparkman Campbell Leigh & Whinston LLP

[57] ABSTRACT

Floribunda rose plant having pure pink color; hard petal substance; production of large flowers in small clusters; being adaptable to greenhouse pot forcing; possessing a long shelf life; and dark green, semi-glossy, disease resistant foliage.

1 Drawing Sheet

The present invention relates to a new and distinct variety of rose plant of the floribunda class which was originated by me by crossing an unnamed seedling (unnamed seedling × Zorina, U.S. Plant Pat. No. 2,231), with the variety 'POULnye', U.S. Plant Pat. No. 8,942. The primary objective of this breeding was to produce a new floribunda rose variety having a pure pink color, hard petal substance, production of flowers in small clusters, adaptable to greenhouse pot forcing, possessing a long shelf life, and large flowers. The objective was substantially achieved, along with other desirable improvements, as evidenced by the following unique combination of characteristics that are outstanding in the new variety and that distinguish it from its parents, as well as from all other varieties of which I am aware:

1. Pure pink color;
2. 2½–3 inch flowers in small clusters;
3. Regularly producing flowers in small clusters;
4. Dark green, semi-glossy foliage;
5. Disease resistance;
6. Fragrance; and
7. Adaptable to greenhouse production 'JACmebub' was bred to be a rose that can be propagated by softwood cuttings, grown in pots in the greenhouse to produce a bud and bloom product for sale in 15–18 weeks time. It was also bred to grow well in the landscape, or as an outdoor pot plant. It achieves these goals quite well. Asexual reproduction of this new variety by cuttings, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling (unnamed seedling× Zorina, U.S. Plant Pat. No. 2,321).

*Pollen parent.*—'POULnye' (U. S. Plant Pat. No. 8,942).

Classification:

*Botanical.*—Rosa hybrida.

*Commercial.*—Floribunda.

FLOWER

Observations made in January 1998, from specimens grown in a greenhouse environment at Somis, Calif.

Blooming habit: Recurrent

Bud:

*Size.*—About one inch long when the petals start to unfurl.

*Form.*—The bud form is pointed ovoid.

*Color.*—When sepals first divide, bud color is Red-Purple Group 59B. When half blown, the upper sides of the petals are close to Red-Purple Group 57D, and the lower sides of the petals are Red-Purple Group 57C.

*Sepals.*—Color: Yellow-Green Group 144A. Surface texture: Smooth, with occasional glands. There are three lightly appendaged sepals. There are two unappendaged sepals with hairy edges.

*Receptacles.*—Color: Green Group 143C. Shape: Funnel. Size: Small, (about 5/16"×¼"). Surface: Smooth.

*Peduncle.*—Length: Long (1¾–2"). Surface: Slightly prickly and glandular. Color: Yellow-Green Group 145A. Strength: Erect; weak; slender.

Bloom:

*Size.*—Medium. Average open size is 2¾ inches.

*Borne.*—Singly and several together in clusters of 3–9 of flat to irregular shape.

*Stems.*—Short; normal strength. Average length is about 8–10 inches.

*Form.*—When first open: High centered. Permanence: Outer petal edges curl under and finish with a moderate degree of quilling.

*Petalage.*—Number of petals under normal conditions: 55–60.

*Color.*—The upper sides of the petals are Red-Purple Group 57D. The reverse sides of the petals are Red-Purple Group 57D. The base of each petal has a small, ⅛", yellow spot (Yellow Group 3C) at its point of attachment. The major color on the upper sides is Red-Purple Group 57D.

*Variegations.*—None.
*Discoloration.*—At the end of the first day: Red-Purple Group 57D. At the end of the third day: Red- Purple Group 68B.
*Fragrance.*—Moderate tea scent.

Petals:
*Texture.*—Leathery.
*Shape.*—Pointed, deltoid.
*Form.*—Edges slightly quilled.
*Arrangement.*—Slightly quartered to imbricated; regularly arranged. Petaloids in the center are few (2 to 5); small and of Red-Purple Group 57D coloration.
*Persistance.*—Petals drop off cleanly before drying.
*Lastingness.*—On the plant: Long (12–14 days). As a cut flower: Not tested.

Reproductive parts:
*Anthers.*—Size: Medium. Quantity: Many. Color: Red Group 42A. Arrangement: Regular around styles; mixed with petaloids.
*Filaments.*—Color: Close to Yellow Group 11A.
*Pollen.*—Color: Yellow Group 6C.
*Styles.*—Color: White Group 155A.
*Stigmas.*—Color: White Group 155A.

Plant:
*Form.*—Bush.
*Growth.*—Vigorous; upright.
*Mature plant in a garden environment.*—Height: 24–30 inches. Width: 20–24 inches.

Foliage: Number of leaflets on normal mid- stem leaves: Five; however, many have seven as well.
*Size.*—Medium (4 inches long×2 inches wide.
*Quantity.*—Normal.
*Color.*—New foliage: Upper surface: Near Yellow-Green Group 144A. Lower surface: Yellow Green Group 146B. Old foliage: Upper surface: Near Green Group 137A. Lower surface: Yellow-Green Group 147B.
*Shape.*—Broadly oval.
*Texture.*—Upper sides: Smooth.
*Edge.*—Serrated.
*Serration.*—Single.
*Petiole rachis.*—Color: Yellow-Green Group 146C.
*Petiole underside.*—Smooth with prickles.
*Stipules.*—Medium ( about ½" long); serrated.
*Disease resistance.*—Resistant to mildew under normal growing conditions at Wasco, Calif., and Somis, Calif.

Wood:
*New wood.*—Color: Yellow-Green Group 146C. Bark: Smooth.
*Old wood.*—Color: Green Group 137C. Bark: Smooth.

Prickles:
*Quantity.*—On main canes from base: Ordinary. On laterals from main canes: Ordinary.
*Form.*—Short (3/16"); straight.
*Color when young.*—Near Greyed-Purple Group 184A rapidly changing to Yellow-Green Group 145C.
*Color when mature.*—Greyed-Yellow Group 160C.

Small prickles:
*Quantity.*—On main stalks: Few to none. On laterals: None.

I claim:

1. A new and distinct variety of floribunda rose plant as herein shown and described, characterized particularly by its pure pink color; hard petal substance; production of large flowers in small clusters; being adaptable to greenhouse pot forcing; possessing a long shelf life; and dark green, semi-glossy, disease resistant foliage.

* * * * *

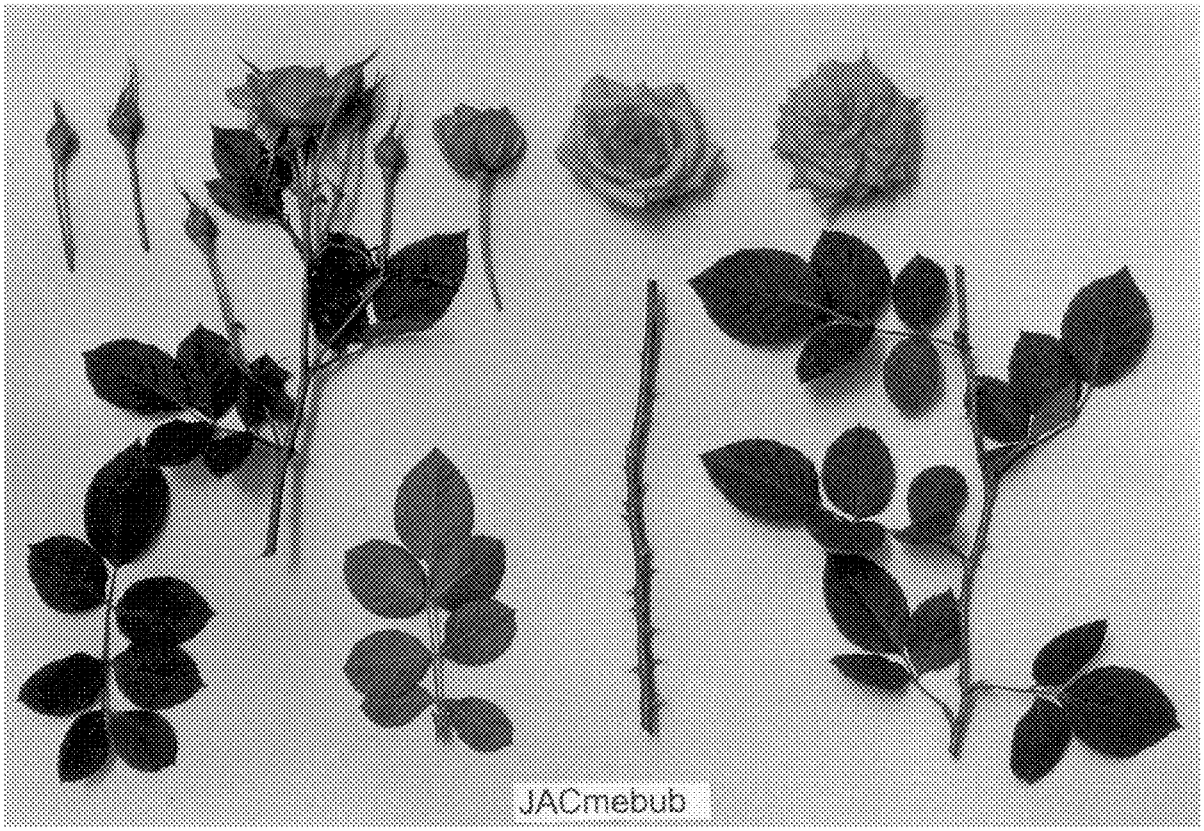
JACmebub